(12) United States Patent
Hsieh

(10) Patent No.: US 6,404,842 B1
(45) Date of Patent: Jun. 11, 2002

(54) METHOD AND APPARATUS FOR IMAGE RECONSTRUCTION IN TWIN HELICAL COMPUTED TOMOGRAPHIC SYSTEMS

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/977,473

(22) Filed: Oct. 15, 2001

(51) Int. Cl.$^7$ ................................................. A61B 6/00
(52) U.S. Cl. .................. 378/4; 378/19; 378/15
(58) Field of Search .................. 378/4, 15, 19, 378/9, 21

(56) References Cited

U.S. PATENT DOCUMENTS

| | | | |
|---|---|---|---|
| 5,513,236 A | * | 4/1996 | Hui ................................ 378/15 |
| 5,559,847 A | * | 9/1996 | Hu et al. ....................... 378/15 |
| 5,708,691 A | | 1/1998 | Zmora |
| 6,233,308 B1 | | 5/2001 | Hsieh |
| 6,263,008 B1 | | 7/2001 | Lai |
| 6,269,139 B1 | | 7/2001 | Hsieh |
| 6,285,732 B1 | | 9/2001 | Hsieh |
| 6,301,325 B1 | | 10/2001 | Besson et al. |
| 6,324,242 B1 | * | 11/2001 | Pan ................................ 378/4 |

* cited by examiner

Primary Examiner—David V. Bruce
Assistant Examiner—Pamela R. Hobden
(74) Attorney, Agent, or Firm—Carl B. Horton, Esq.; Armstrong Teasdale LLP

(57) ABSTRACT

A method for weighting projection data is provided. The method includes helically twin beam scanning an object at a selected pitch to acquire a first data sample from a first detector row and a second data sample from a second detector row. The first data sample includes first conjugate data and first two pi data. The second data sample includes second conjugate data and second two pi data. The first conjugate data and the second conjugate data are conjugate each other, and the first two pi data and the second two pi data are two $\pi$ projection angle apart. The method also includes identifying a center view of the first conjugate data and the second conjugate data, and weighting at least one of the first conjugate data, the second conjugate data, the first two pi data, and the second two pi data inverse to the identified center view.

30 Claims, 2 Drawing Sheets

METHOD AND APPARATUS FOR IMAGE RECONSTRUCTION IN TWIN HELICAL COMPUTED TOMOGRAPHIC SYSTEMS

BACKGROUND OF THE INVENTION

This invention relates to tomographic imaging, and more particularly to methods and apparatus for reducing aliasing artifacts in computerized tomographic (CT) imaging in a twin beam imaging system.

In at least one known CT imaging system configuration, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed.

Reconstruction algorithms for helical scanning typically use helical weighing algorithms which weight the collected data as a function of view angle and detector channel index. Specifically, prior to filtered back projection, the data is weighted according to a helical weighing factor, which is a function of both the gantry angle and detector angle. The helical weighting algorithms also scale the data according to a scaling factor, which is a function of the distance between the x-ray source and the object. The weighted and scaled data is then processed to generate CT numbers and to construct an image that corresponds to a two dimensional slice taken through the object.

In some known clinical scans, projection weighting prior to image reconstruction is performed. For example, halfscan weighting has been implemented to shorten scan time by approximately 40%. Underscan weighting is used to suppress patient motion in axial scan protocols. On the other hand, helical weightings ("High Quality" or HQ mode, and "High Speed" or HS mode, for example) have been used to avoid artifacts resulting from constant table translation during a scan. However, because of a lack of quarter-detector offset, halfscan sampling without focal spot deflection typically does not produce aliasing-free images for high-resolution kernels.

BRIEF SUMMARY OF THE INVENTION

In one aspect, a method for weighting projection data is provided. The method includes helically twin beam scanning an object at a selected pitch to acquire a first data sample from a first detector row and a second data sample from a second detector row. The first data sample includes first conjugate data and first two pi data. The second data sample includes second conjugate data and second two pi data. The first conjugate data and the second conjugate data are conjugate each other, and the first two pi data and the second two pi data are two π projection angle apart. The method also includes identifying a center view of the first conjugate data and the second conjugate data, and weighting at least one of the first conjugate data, the second conjugate data, the first two pi data, and the second two pi data inverse to the identified center view.

In another aspect, a method for weighting projection data is provided. The method includes helically twin beam scanning an object at a selected pitch to acquire a first data sample from a first detector row and a second data sample from a second detector row. The first data sample includes first conjugate data and first two pi data. The second data sample includes second conjugate data and second two pi data. The first conjugate data and the second conjugate data are conjugate each other, and the first two pi data and the second two pi data are two π projection angle apart. The method also includes identifying a center view of the first conjugate data and the second conjugate data, wherein the center view is π/p from β1 and π/p from β2. Wherein p is a helical pitch, β1 is the projection angle at which the first detector row intersects a plane of reconstruction, and β2 is the projection angle at which the second detector row intersects the plane of reconstruction. The method also includes weighting the first data sample according to $$w_1(\gamma, \beta) = \begin{cases} \left(\dfrac{\beta - \beta2 + 2\pi}{\beta1 - \beta2 + 2\pi}\right)\left[\dfrac{(1 - 2\alpha)(\beta + 2\pi - \beta0 + 2\gamma)}{\pi + 2\gamma} + \alpha\right] & \beta2 - 2\pi \leq \beta \leq \beta0 - \pi \\ \left(\dfrac{\beta - \beta2 + 2\pi}{\beta1 - \beta2 + 2\pi}\right)\left[\dfrac{(1 - 2\alpha)(\beta0 - 2\gamma - \beta)}{\pi - 2\gamma} + \alpha\right] & \beta0 - \pi \leq \beta \leq \beta1 \\ \left(\dfrac{\beta2 - \beta}{\beta2 - \beta1}\right)\left[\dfrac{(1 - 2\alpha)(\beta0 - 2\gamma - \beta)}{\pi - 2\gamma} + \alpha\right] & \beta1 \leq \beta < \beta0 - 2\gamma \\ \left(\dfrac{\beta2 - \beta}{\beta2 - \beta1}\right)\left[\dfrac{(1 - 2\alpha)(\beta - \beta0 + 2\gamma)}{\pi + 2\gamma} + \alpha\right] & \beta0 - 2\gamma \leq \beta < \beta2 \end{cases}$$

and weighting the second data sample according to $$w_2(\gamma, \beta) = \begin{cases} \left(\frac{\beta - \beta_1}{\beta_2 - \beta_1}\right)\left[\frac{(1-2\alpha)(\beta_0 - 2\gamma - \beta)}{\pi - 2\gamma}\right] & \beta_1 \le \beta \le \beta_0 - 2\gamma \\ \left(\frac{\beta - \beta_1}{\beta_2 - \beta_1}\right)\left[\frac{(1-2\alpha)(\beta - \beta_0 + 2\gamma)}{\pi + 2\gamma} + \alpha\right] & \beta_0 - 2\gamma \le \beta < \beta_2 \\ \left(\frac{\beta_1 + 2\pi - \beta}{\beta_1 + \pi - \beta_2}\right)\left[\frac{(1-2\alpha)(\beta - \beta_0 + 2\gamma)}{\pi + 2\gamma} + \alpha\right] & \beta_2 \le \beta < \beta_0 + \pi \\ \left(\frac{\beta_1 + 2\pi - \beta}{\beta_1 + \pi - \beta_2}\right)\left[\frac{(1-2\alpha)(\beta_0 - 2\gamma - \beta + 2\pi)}{\pi - 2\gamma} + \alpha\right] & \beta_0 + \pi \le \beta < \beta_1 + 2\pi \end{cases}$$

where β is a projection angle, β0 is the identified center view, γ is a fan angle, and α is a relative strength parameter.

In a further aspect, a twin beam computerized tomographic (CT) imaging system for imaging an object is provided. The imaging system includes a detector array, at least one radiation source, and a computer coupled to the detector array and radiation source. The computer is configured to helically twin beam scan an object at a selected pitch to acquire a first data sample from a first detector row and a second data sample from a second detector row. The first data sample including first conjugate data and first two pi data. The second data sample including second conjugate data and second two pi data. The first conjugate data and the second conjugate data are conjugate each other, and the first two pi data and the second two pi data are two π projection angle apart. The computer is also configured to identify a center view of the first conjugate data and the second conjugate data, and weight at least one of the first conjugate data, the second conjugate data, the first two pi data, and the second two pi data inverse to the identified center view. The computer is also configured to filter and backproject the weighted projection data to generate an image of the object.

In one aspect, a twin beam computerized tomographic (CT) imaging system for imaging an object is provided. The imaging system includes a detector array, at least one radiation source, and a computer coupled to the detector array and radiation source. The computer is configured to helically twin beam scan an object at a selected pitch to acquire a first data sample from a first detector row and a second data sample from a second detector row. The first data sample includes first conjugate data and first two pi data. The second data sample includes second conjugate data and second two pi data. The first conjugate data and the second conjugate data are conjugate each other, and the first two pi data and the second two pi data are two π projection angle apart. The computer is also configured to identify a center view of the first conjugate data and the second conjugate data, weight the first data sample according to and weight the second data sample according to $$w_2(\gamma, \beta) = \begin{cases} \left(\frac{\beta - \beta_1}{\beta_2 - \beta_1}\right)\left[\frac{(1-2\alpha)(\beta_0 - 2\gamma - \beta)}{\pi - 2\gamma}\right] & \beta_1 \le \beta \le \beta_0 - 2\gamma \\ \left(\frac{\beta - \beta_1}{\beta_2 - \beta_1}\right)\left[\frac{(1-2\alpha)(\beta - \beta_0 + 2\gamma)}{\pi + 2\gamma} + \alpha\right] & \beta_0 - 2\gamma \le \beta < \beta_2 \\ \left(\frac{\beta_1 + 2\pi - \beta}{\beta_1 + \pi - \beta_2}\right)\left[\frac{(1-2\alpha)(\beta - \beta_0 + 2\gamma)}{\pi + 2\gamma} + \alpha\right] & \beta_2 \le \beta < \beta_0 + \pi \\ \left(\frac{\beta_1 + 2\pi - \beta}{\beta_1 + \pi - \beta_2}\right)\left[\frac{(1-2\alpha)(\beta_0 - 2\gamma - \beta + 2\pi)}{\pi - 2\gamma} + \alpha\right] & \beta_0 + \pi \le \beta < \beta_1 + 2\pi \end{cases}$$

where β is a projection angle, β0 is the identified center view, β1 is the projection angle at which the first detector row intersects a plane of reconstruction, β2 is the projection angle at which the second detector row intersects the plane of reconstruction, γ is a fan angle, and α is a relative strength parameter.

In another aspect, a computer readable medium encoded with a program executable by a computer for reconstructing a three-dimensional dataset representative of an imaged object is provided. The program is configured to instruct the computer to helically twin beam scan an object at a selected pitch to acquire a first data sample from a first detector row and a second data sample from a second detector row. The first data sample including first conjugate data and first two pi data. The second data sample including second conjugate data and second two pi data. The first conjugate data and the second conjugate data are conjugate each other, and the first two pi data and the second two pi data are two π projection angle apart. The program is also configured to instruct the computer to identify a center view of the first conjugate data and the second conjugate data, and weight at least one of the first conjugate data, the second conjugate data, the first two pi data, and the second two pi data inverse to the identified center view. The program is also configured to instruct the computer to filter and backproject the weighted projection data to generate an image of the object.

In a further aspect, a computer readable medium encoded with a program executable by a computer for reconstructing a three-dimensional dataset representative of an imaged object is provided. The program is configured to instruct the computer to helically twin beam scan an object at a selected pitch to acquire a first data sample from a first detector row and a second data sample from a second detector row. The first data sample includes first conjugate data and first two pi data. The second data sample includes second conjugate data and second two pi data. The first conjugate data and the second conjugate data are conjugate each other, and the first two pi data and the second two pi data are two π projection $$w_1(\gamma, \beta) = \begin{cases} \left(\frac{\beta - \beta_2 + 2\pi}{\beta_1 - \beta_2 + 2\pi}\right)\left[\frac{(1-2\alpha)(\beta + 2\pi - \beta_0 + 2\gamma)}{\pi + 2\gamma} + \alpha\right] & \beta_2 - 2\pi \le \beta \le \beta_0 - \pi \\ \left(\frac{\beta - \beta_2 + 2\pi}{\beta_1 - \beta_2 + 2\pi}\right)\left[\frac{(1-2\alpha)(\beta_0 - 2\gamma - \beta)}{\pi - 2\gamma} + \alpha\right] & \beta_0 - \pi \le \beta \le \beta_1 \\ \left(\frac{\beta_2 - \beta}{\beta_2 - \beta_1}\right)\left[\frac{(1-2\alpha)(\beta_0 - 2\gamma - \beta)}{\pi - 2\gamma} + \alpha\right] & \beta_1 \le \beta < \beta_0 - 2\gamma \\ \left(\frac{\beta_2 - \beta}{\beta_2 - \beta_1}\right)\left[\frac{(1-2\alpha)(\beta - \beta_0 + 2\gamma)}{\pi + 2\gamma} + \alpha\right] & \beta_0 - 2\gamma \le \beta < \beta_2 \end{cases}$$

angle apart. The program is also configured to instruct the computer to identify a center view of the first conjugate data and the second conjugate data; wherein the center view is π/p from a first projection region and π/p from a third projection region, wherein p is a helical pitch. The program is also configured to instruct the computer to weight the first data sample according to $$w_1(\gamma,\beta) = \begin{cases} \left(\dfrac{\beta-\beta 2+2\pi}{\beta 1-\beta 2+2\pi}\right)\left[\dfrac{(1-2\alpha)(\beta+2\pi-\beta 0+2\gamma)}{\pi+2\gamma}+\alpha\right] & \beta 2-2\pi \le \beta \le \beta 0-\pi \\ \left(\dfrac{\beta-\beta 2+2\pi}{\beta 1-\beta 2+2\pi}\right)\left[\dfrac{(1-2\alpha)(\beta 0-2\gamma-\beta)}{\pi-2\gamma}+\alpha\right] & \beta 0-\pi \le \beta \le \beta 1 \\ \left(\dfrac{\beta 2-\beta}{\beta 2-\beta 1}\right)\left[\dfrac{(1-2\alpha)(\beta 0-2\gamma-\beta)}{\pi-2\gamma}+\alpha\right] & \beta 1 \le \beta < \beta 0-2\gamma \\ \left(\dfrac{\beta 2-\beta}{\beta 2-\beta 1}\right)\left[\dfrac{(1-2\alpha)(\beta-\beta 0+2\gamma)}{\pi+2\gamma}+\alpha\right] & \beta 0-2\gamma \le \beta < \beta 2 \end{cases}$$

and weight the second data sample according to $$w_2(\gamma,\beta) = \begin{cases} \left(\dfrac{\beta-\beta 1}{\beta 2-\beta 1}\right)\left[\dfrac{(1-2\alpha)(\beta 0-2\gamma-\beta)}{\pi-2\gamma}\right] & \beta 1 \le \beta \le \beta 0-2\gamma \\ \left(\dfrac{\beta-\beta 1}{\beta 2-\beta 1}\right)\left[\dfrac{(1-2\alpha)(\beta-\beta 0+2\gamma)}{\pi+2\gamma}+\alpha\right] & \beta 0-2\gamma \le \beta < \beta 2 \\ \left(\dfrac{\beta 1+2\pi-\beta}{\beta 1+\pi-\beta 2}\right)\left[\dfrac{(1-2\alpha)(\beta-\beta 0+2\gamma)}{\pi+2\gamma}+\alpha\right] & \beta 2 \le \beta < \beta 0+\pi \\ \left(\dfrac{\beta 1+2\pi-\beta}{\beta 1+\pi-\beta 2}\right)\left[\dfrac{(1-2\alpha)(\beta 0-2\gamma-\beta+2\pi)}{\pi-2\gamma}+\alpha\right] & \beta 0+\pi \le \beta < \beta 1+2\pi \end{cases}$$

where ,β is a projection angle, β0 is the identified center view, ⊕1 is the projection angle at which the first detector row intersects a plane of reconstruction, β2 is the projection angle at which the second detector row intersects the plane of reconstruction, γ is a fan angle, and α is a relative strength parameter.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
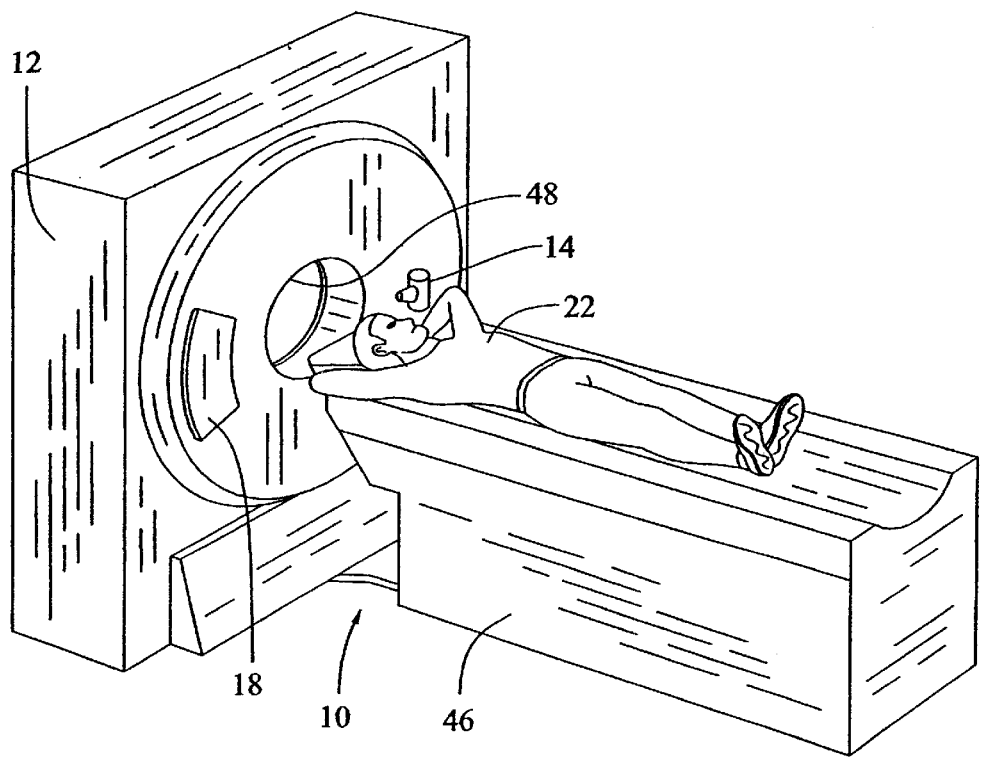
FIG. 1 is a pictorial view of a CT imaging system.
Figure 2:
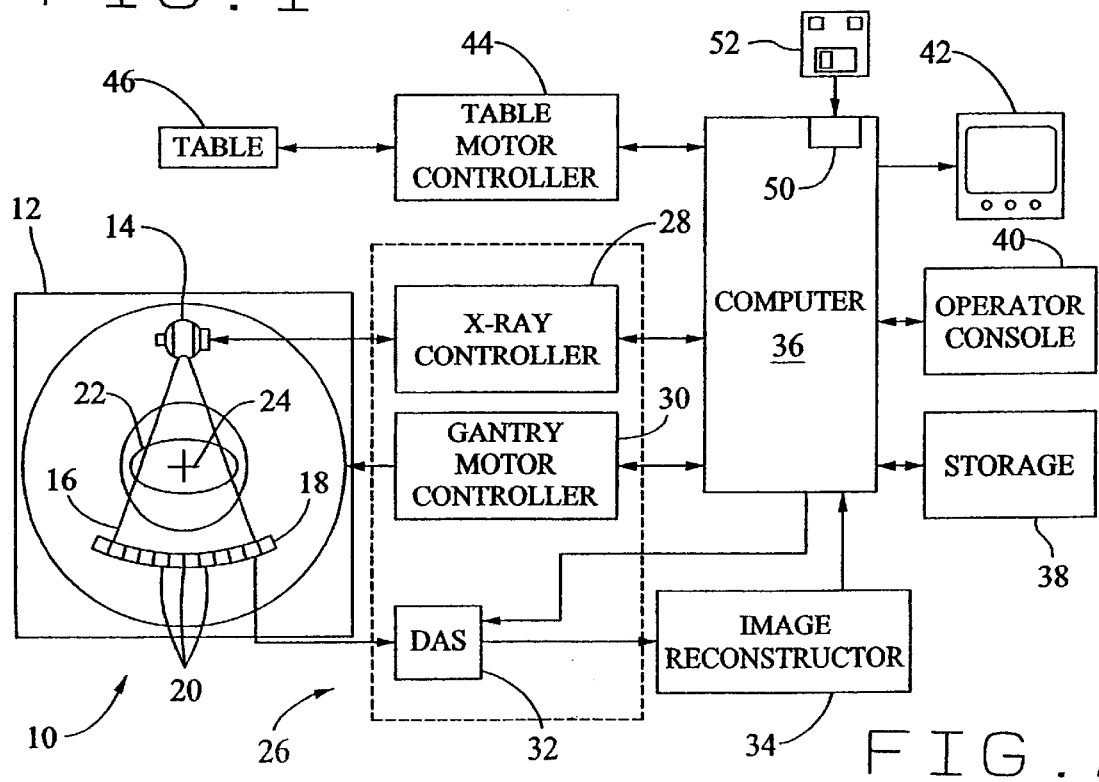
FIG. 2 is a block schematic diagram of the system illustrated in FIG. 1.

Referring to FIGS. 1 and 2, a twin beam computed tomography (CT) imaging system 10 is shown as including a gantry 12 representative of a "third generation" twin beam CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 is fabricated in a multi-slice configuration such that detector array 18 has a plurality of rows of detector elements or cells 20, only one of which is shown in FIG. 2. During a twin beam helical scan, data is acquired from two detector rows at the same time. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a storage device 38. Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48. In a helical scan as performed in one embodiments of the present invention, table 46 moves while projection data is being collected and gantry 12 is rotating. The "helical pitch" is a measure of the amount of movement of table 46 per rotation of gantry 12.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Computer 36 and/or image reconstructor 34 of imaging system 10, either alone or in combination, provide the processing power necessary to perform the computational steps described herein in at least one embodiment of the present invention. Instructions for performing the computational steps are stored in an associated memory, such as storage device 38, read only or read/write memory (not shown separately in FIG. 1), or media 52.

Figure 3:
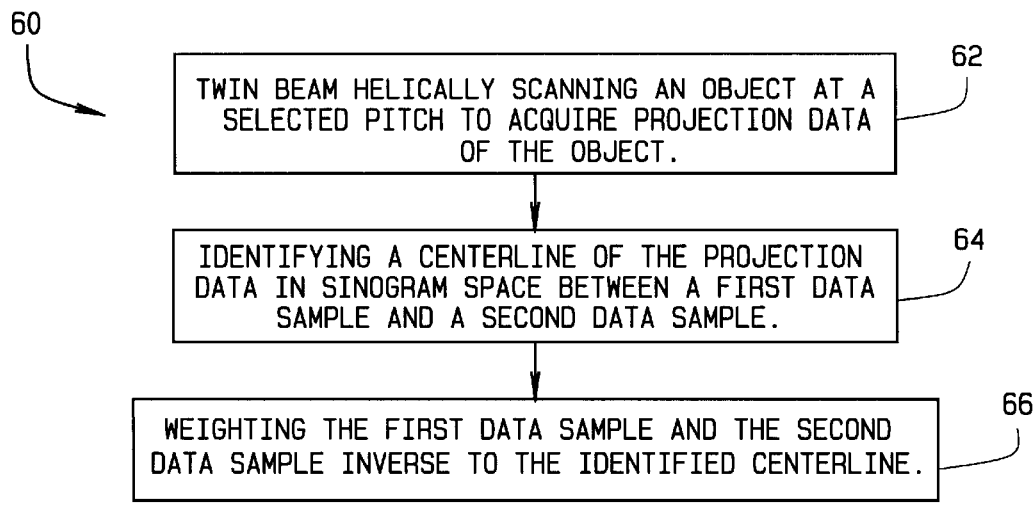
FIG. 3 is a flow diagram of a method for weighting projection data.

FIG. 3 is a flowchart illustrating an exemplary method 60 for weighting projection data. Method 60 includes twin beam helically scanning 62 an object 12 (shown in FIG. 1) at a selected pitch (p) to acquire projection data of object 22, identifying 64 a center view of the projection data in sinogram space of a first data sample (not shown in FIG. 3) and a second data sample (not shown in FIG. 3) as explained in greater detail below. Method 60 also includes weighting 66 the first data sample and the second data sample inverse to the identified center view.

Figure 4:
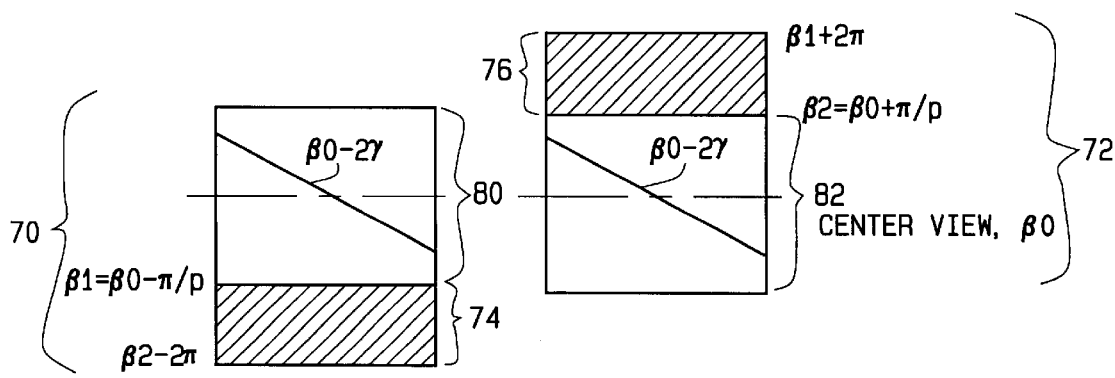
FIG. 4 is a sinogram view of a first projection sample and a second projection sample.

FIG. 4 is a sinogram view of a first data sample 70 which is collected from a first detector row (not shown). A second projection data sample 72 is collected from a second detector row (not shown). The projection angles β at which the two detector rows intersect a plane of reconstruction (POR) are denoted by β1 (first projection angle) and β2 (second projection angle), respectively. First data sample 70 includes first two pi data 74 which is collected between β2−2π and , β1. Second data sample 72 includes second two pi data 76 which is collected between β1+2π and β2. First two pi data 74 and second two pi data 76 constitute data collected two π apart in projection angle.

First data sample 70 also includes first conjugate data 80 representing data collected between β1 and β2. Second data sample 72 also includes second conjugate data 82 representing data collected between β1 and β2. First conjugate data 80 and second conjugate data 82 are acquired from two detector rows with the same projection angle (β). Therefore, first conjugate data 80 and second conjugate data 82 are conjugate to each other.

Identifying 64 a center view (β0) includes identifying 64 a center view that is πp from β1 and πp from β2 wherein p can be variably selected by an operator. Accordingly, the center view β0 bisects the locations at which the two detector rows intersect the plane of reconstruction.

Additional weights, such as inverse-helical weights, are applied to the z-location interpolation weights to compensate for the quality of the interpolated samples, i.e. first conjugate data 80 and second conjugate data 82, because the interpolated samples located near the center view are worst in terms of quality. Inverse weighting herein means weighting data collected near β0 less than data collected away from β0.

In one embodiment, using an inverse helical weight, weighting 66 first data sample 70 and second data sample 72 inverse to the identified center view β0 includes weighting first two pi data 74 differently than first conjugate data 80, and weighting second two pi data 76 differently than second conjugate data 82 because the accuracy of interpolation, and the slice sensitivity profile, degrades as the distance from the measured samples from the interpolation location increases.

In one embodiment, first data sample 70 is weighted according to:

$$w_1(\gamma, \beta) = \begin{cases} \left(\frac{\beta - \beta2 + 2\pi}{\beta1 - \beta2 + 2\pi}\right)\left[\frac{(1-2\alpha)(\beta + 2\pi - \beta0 + 2\gamma)}{\pi + 2\gamma} + \alpha\right] & \beta2 - 2\pi \le \beta \le \beta0 - \pi \\ \left(\frac{\beta - \beta2 + 2\pi}{\beta1 - \beta2 + 2\pi}\right)\left[\frac{(1-2\alpha)(\beta0 - 2\gamma - \beta)}{\pi - 2\gamma} + \alpha\right] & \beta0 - \pi \le \beta \le \beta1 \\ \left(\frac{\beta2 - \beta}{\beta2 - \beta1}\right)\left[\frac{(1-2\alpha)(\beta0 - 2\gamma - \beta)}{\pi - 2\gamma} + \alpha\right] & \beta1 \le \beta < \beta0 - 2\gamma \\ \left(\frac{\beta2 - \beta}{\beta2 - \beta1}\right)\left[\frac{(1-2\alpha)(\beta - \beta0 + 2\gamma)}{\pi + 2\gamma} + \alpha\right] & \beta0 - 2\gamma \le \beta < \beta2 \end{cases}$$

and second data sample 72 is weighted according to:

$$w_2(\gamma, \beta) = \begin{cases} \left(\frac{\beta - \beta1}{\beta2 - \beta1}\right)\left[\frac{(1-2\alpha)(\beta0 - 2\gamma - \beta)}{\pi - 2\gamma}\right] & \beta1 \le \beta \le \beta0 - 2\gamma \\ \left(\frac{\beta - \beta1}{\beta2 - \beta1}\right)\left[\frac{(1-2\alpha)(\beta - \beta0 + 2\gamma)}{\pi + 2\gamma} + \alpha\right] & \beta0 - 2\gamma \le \beta < \beta2 \\ \left(\frac{\beta1 + 2\pi - \beta}{\beta1 + \pi - \beta2}\right)\left[\frac{(1-2\alpha)(\beta - \beta0 + 2\gamma)}{\pi + 2\gamma} + \alpha\right] & \beta2 \le \beta < \beta0 + \pi \\ \left(\frac{\beta1 + 2\pi - \beta}{\beta1 + \pi - \beta2}\right)\left[\frac{(1-2\alpha)(\beta0 - 2\gamma - \beta + 2\pi)}{\pi - 2\gamma} + \alpha\right] & \beta0 + \pi \le \beta < \beta1 + 2\pi \end{cases}$$

where α is a parameter that adjusts a relative strength of the inverse-helical weights and is between approximately 0 and approximately 0.5. In another embodiment, α is between approximately 0.1 and approximately 0.4. In use, the smaller the value of α, the less contribution comes from the samples that are located closer to β0. Alternatively, a smaller value of α represents less contribution of quarter-detector offset to compensate for the aliasing artifacts in high-resolution algorithms.

In another embodiment, other inverse weights, such as, but not limited to, inverse-underscan weights, inverse-HE weights, or inverse-general halfscan weights can be applied to adjust for the tradeoff between slice-sensitivity-profile and aliasing artifacts.

While the invention has been described in terms of various specific embodiments, those skilled in the art will recognize that the invention can be practiced with modification within the spirit and scope of the claims.

What is claimed is:

1. A method for weighting projection data, said method comprising:

helically twin beam scanning an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;

identifying a center view of the first conjugate data and the second conjugate data; and weighting at least one of the first conjugate data, the second conjugate data, the first two pi data, and the second two pi data inverse to the identified center view.

2. A claim in accordance with claim 1 wherein the center view is π/p from β1 and π/p from β2, wherein p is a helical pitch, β1 is the projection angle at which the first detector row intersects a plane of reconstruction, and β2 is the projection angle at which the second detector row intersects the plane of reconstruction.

3. A method in accordance with claim 1 wherein weighting at least one of the first conjugate data, the second conjugate data, the first two pi data, and the second two pi data inverse to the identified center view comprises weighting the first data sample according to:

$$w_1(\gamma, \beta) = \begin{cases} \left(\frac{\beta - \beta 2 + 2\pi}{\beta 1 - \beta 2 + 2\pi}\right)\left[\frac{(1 - 2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\frac{\beta - \beta 2 + 2\pi}{\beta 1 - \beta 2 + 2\pi}\right)\left[\frac{(1 - 2\alpha)(\beta 0 - 2\gamma - \beta)}{\pi - 2\gamma} + \alpha\right] & \beta 0 - \pi \leq \beta \leq \beta 1 \\ \left(\frac{\beta 2 - \beta}{\beta 2 - \beta 1}\right)\left[\frac{(1 - 2\alpha)(\beta 0 - 2\gamma - \beta)}{\pi - 2\gamma} + \alpha\right] & \beta 1 \leq \beta < \beta 0 - 2\gamma \\ \left(\frac{\beta 2 - \beta}{\beta 2 - \beta 1}\right)\left[\frac{(1 - 2\alpha)(\beta - \beta 0 + 2\gamma)}{\pi + 2\gamma} + \alpha\right] & \beta 0 - 2\gamma \leq \beta < \beta 2 \end{cases}$$

where

β is a projection angle;

β0 is the identified center view;

β1 is the projection angle at which the first detector row intersects a plane of reconstruction;

β2 is the projection angle at which the second detector row intersects the plane of reconstruction;

γ is a fan angle; and

α is a relative strength parameter.

4. A method in accordance with claim 1 wherein weighting at least one of the first conjugate data, the second conjugate data, the first two pi data, and the second two pi data inverse to the identified center view comprises weighting the first conjugate data and the second conjugate data inverse to the identified center view.

5. A method in accordance with claim 4 wherein weighting the second conjugate data inverse to the identified center view comprises weighting the second data sample according to:

$$w_2(\gamma, \beta) = \begin{cases} \left(\frac{\beta - \beta 1}{\beta 2 - \beta 1}\right)\left[\frac{(1 - 2\alpha)(\beta 0 - 2\gamma - \beta)}{\pi - 2\gamma}\right] & \beta 1 \leq \beta \leq \beta 0 - 2\gamma \\ \left(\frac{\beta - \beta 1}{\beta 2 - \beta 1}\right)\left[\frac{(1 - 2\alpha)(\beta - \beta 0 + 2\gamma)}{\pi + 2\gamma} + \alpha\right] & \beta 0 - 2\gamma \leq \beta < \beta 2 \\ \left(\frac{\beta 1 + 2\pi - \beta}{\beta 1 + \pi - \beta 2}\right)\left[\frac{(1 - 2\alpha)(\beta - \beta 0 + 2\gamma)}{\pi + 2\gamma} + \alpha\right] & \beta 2 \leq \beta < \beta 0 + \pi \\ \left(\frac{\beta 1 + 2\pi - \beta}{\beta 1 + \pi - \beta 2}\right)\left[\frac{(1 - 2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where

β is a projection angle;

β0 is the identified center view;

β1 is the projection angle at which the first detector row intersects a plane of reconstruction;

β2 is the projection angle at which the second detector row intersects the plane of reconstruction;

γ is a fan angle; and

α is a relative strength parameter.

6. A method in accordance with claim 3 wherein α is between approximately 0 and approximately 0.5.

7. A method in accordance with claim 5 wherein α is between approximately 0 and approximately 0.5.

8. A method in accordance with claim 1 wherein weighting at least one of the first conjugate data, the second conjugate data, the first two pi data, and the second two pi data inverse to the identified center view comprises weighting at least one of the first conjugate data, the second conjugate data, the first two pi data, and the second two pi data with one of an inverse helical interpolation weight, an inverse-underscan weight, an inverse helical extrapolation weight, and an inverse general halfscan weight.

9. A method in accordance with claim 4 wherein weighting the first conjugate data inverse to the identified center view comprises weighting the first data sample according to $$w_1(\gamma, \beta) = \begin{cases} \left(\frac{\beta - \beta 2 + 2\pi}{\beta 1 - \beta 2 + 2\pi}\right)\left[\frac{(1 - 2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\frac{\beta - \beta 2 + 2\pi}{\beta 1 - \beta 2 + 2\pi}\right)\left[\frac{(1 - 2\alpha)(\beta 0 - 2\gamma - \beta)}{\pi - 2\gamma} + \alpha\right] & \beta 0 - \pi \leq \beta \leq \beta 1 \\ \left(\frac{\beta 2 - \beta}{\beta 2 - \beta 1}\right)\left[\frac{(1 - 2\alpha)(\beta 0 - 2\gamma - \beta)}{\pi - 2\gamma} + \alpha\right] & \beta 1 \leq \beta < \beta 0 - 2\gamma \\ \left(\frac{\beta 2 - \beta}{\beta 2 - \beta 1}\right)\left[\frac{(1 - 2\alpha)(\beta - \beta 0 + 2\gamma)}{\pi + 2\gamma} + \alpha\right] & \beta 0 - 2\gamma \leq \beta < \beta 2 \end{cases}$$

and wherein weighting the second conjugate data inverse to the identified center view comprises weighting the second data sample according to $$w_2(\gamma, \beta) = \begin{cases} \left(\frac{\beta - \beta 1}{\beta 2 - \beta 1}\right)\left[\frac{(1-2\alpha)(\beta 0 - 2\gamma - \beta)}{\pi - 2\gamma}\right] & \beta 1 \leq \beta \leq \beta 0 - 2\gamma \\ \left(\frac{\beta - \beta 1}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \\ \left(\frac{\beta 1 + 2\pi - \beta}{\beta 1 + \pi - \beta 2}\right)\left[\frac{(1-2\alpha)(\beta - \beta 0 + 2\gamma)}{\pi + 2\gamma} + \alpha\right] & \beta 2 \leq \beta < \beta 0 + \pi \\ \left(\frac{\beta 1 + 2\pi - \beta}{\beta 1 + \pi - \beta 2}\right)\left[\frac{(1-2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where

β is a projection angle;

β0 is the identified center view;

β1 is the projection angle at which the first detector row intersects a plane of reconstruction;

β1 is the projection angle at which the second detector row intersects the plane of reconstruction;

γ is a fan angle;

the first conjugate data and the second conjugate data are acquired between β1 and β2;

the first two pi data acquired between β2−2π and β1;

the second two pi data acquired between β2 and β1+2π, and

α is a relative strength parameter.

10. A method for weighting projection data, said method comprising:

helically twin beam scanning an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;

identifying a center view of the first conjugate data and the second conjugate data, wherein the center view is β/p from β1 and π/p from β2, wherein p is a helical pitch, β1 is the projection angle at which the first detector row intersects a plane of reconstruction, and β2 is the projection angle at which the second detector row intersects the plane of reconstruction; and weighting the first data sample according to:

and weighting the second data sample according to:

$$w_2(\gamma, \beta) = \begin{cases} \left(\frac{\beta - \beta 1}{\beta 2 - \beta 1}\right)\left[\frac{(1-2\alpha)(\beta 0 - 2\gamma - \beta)}{\pi - 2\gamma}\right] & \beta 1 \leq \beta \leq \beta 0 - 2\gamma \\ \left(\frac{\beta - \beta 1}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \\ \left(\frac{\beta 1 + 2\pi - \beta}{\beta 1 + \pi - \beta 2}\right)\left[\frac{(1-2\alpha)(\beta - \beta 0 + 2\gamma)}{\pi + 2\gamma} + \alpha\right] & \beta 2 \leq \beta < \beta 0 + \pi \\ \left(\frac{\beta 1 + 2\pi - \beta}{\beta 1 + \pi - \beta 2}\right)\left[\frac{(1-2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where

β is a projection angle;

β0 is the identified center view;

γ is a fan angle; and

α is a relative strength parameter.

11. A twin beam computerized tomographic (CT) imaging system for imaging an object, said imaging system comprising:

a detector array;

at least one radiation source; and a computer coupled to said detector array and radiation source and configured to:

helically twin beam scan an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;

identify a center view of the first conjugate data and the second conjugate data;

weight at least one of the first conjugate data, the second conjugate data, the first two pi data, and the second two pi data inverse to the identified center view; and filter and backproject the weighted projection data to generate an image of the object.

12. A system in accordance with claim 11 wherein to identify a center view, said computer further configured to identify a center view wherein the center view is π/p from β1 and π/p from β2, wherein p is a helical pitch, β1 is the projection angle at which the first detector row intersects a plane of reconstruction, and β2 is the projection angle at which the second detector row intersects the plane of reconstruction.

$$w_1(\gamma, \beta) = \begin{cases} \left(\frac{\beta - \beta 2 + 2\pi}{\beta 1 - \beta 2 + 2\pi}\right)\left[\frac{(1-2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\frac{\beta - \beta 2 + 2\pi}{\beta 1 - \beta 2 + 2\pi}\right)\left[\frac{(1-2\alpha)(\beta 0 - 2\gamma - \beta)}{\pi - 2\gamma} + \alpha\right] & \beta 0 - \pi \leq \beta \leq \beta 1 \\ \left(\frac{\beta 2 - \beta}{\beta 2 - \beta 1}\right)\left[\frac{(1-2\alpha)(\beta 0 - 2\gamma - \beta)}{\pi - 2\gamma} + \alpha\right] & \beta 1 \leq \beta < \beta 0 - 2\gamma \\ \left(\frac{\beta 2 - \beta}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \end{cases}$$

13. A system in accordance with claim 11 wherein said computer further configured to weight the first data sample according to:

$$w_1(\gamma, \beta) = \begin{cases} \left(\dfrac{\beta - \beta 2 + 2\pi}{\beta 1 - \beta 2 + 2\pi}\right)\left[\dfrac{(1-2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\dfrac{\beta - \beta 2 + 2\pi}{\beta 1 - \beta 2 + 2\pi}\right)\left[\dfrac{(1-2\alpha)(\beta 0 - 2\gamma - \beta)}{\pi - 2\gamma} + \alpha\right] & \beta 0 - \pi \leq \beta \leq \beta 1 \\ \left(\dfrac{\beta 2 - \beta}{\beta 2 - \beta 1}\right)\left[\dfrac{(1-2\alpha)(\beta 0 - 2\gamma - \beta)}{\pi - 2\gamma} + \alpha\right] & \beta 1 \leq \beta < \beta 0 - 2\gamma \\ \left(\dfrac{\beta 2 - \beta}{\beta 2 - \beta 1}\right)\left[\dfrac{(1-2\alpha)(\beta - \beta 0 + 2\gamma)}{\pi + 2\gamma} + \alpha\right] & \beta 0 - 2\gamma \leq \beta < \beta 2 \end{cases}$$

where
- $\beta$ is a projection angle;
- $\beta 0$ is the identified center view;
- $\beta 1$ is the projection angle at which the first detector row intersects a plane of reconstruction;
- $\beta 2$ is the projection angle at which the second detector row intersects the plane of reconstruction;
- $\gamma$ is a fan angle; and
- $\alpha$ is a relative strength parameter.

14. A system in accordance with claim 11 said computer further configured to weight the first conjugate data and the second conjugate data inverse to the identified center view.

15. A system in accordance with claim 14 wherein to weight the second conjugate data inverse to the identified center view, said computer further configured to weight the second data sample according to:

$$w_2(\gamma, \beta) = \begin{cases} \left(\dfrac{\beta - \beta 1}{\beta 2 - \beta 1}\right)\left[\dfrac{(1-2\alpha)(\beta 0 - 2\gamma - \beta)}{\pi - 2\gamma}\right] & \beta 1 \leq \beta \leq \beta 0 - 2\gamma \\ \left(\dfrac{\beta - \beta 1}{\beta 2 - \beta 1}\right)\left[\dfrac{(1-2\alpha)(\beta - \beta 0 + 2\gamma)}{\pi + 2\gamma} + \alpha\right] & \beta 0 - 2\gamma \leq \beta < \beta 2 \\ \left(\dfrac{\beta 1 + 2\pi - \beta}{\beta 1 + \pi - \beta 2}\right)\left[\dfrac{(1-2\alpha)(\beta - \beta 0 + 2\gamma)}{\pi + 2\gamma} + \alpha\right] & \beta 2 \leq \beta < \beta 0 + \pi \\ \left(\dfrac{\beta 1 + 2\pi - \beta}{\beta 1 + \pi - \beta 2}\right)\left[\dfrac{(1-2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where
- $\beta$ is a projection angle;
- $\beta 0$ is the identified center view;
- $\beta 1$ is the projection angle at which the first detector row intersects a plane of reconstruction;
- $\beta 2$ is the projection angle at which the second detector row intersects the plane of reconstruction;
- $\gamma$ is a fan angle; and
- $\alpha$ is a relative strength parameter.

16. A system in accordance with claim 13 wherein $\alpha$ is between approximately 0 and approximately 0.5.

17. A system in accordance with claim 15 wherein $\alpha$ is between approximately 0 and approximately 0.5.

18. A system in accordance with claim 11 wherein to weight at least one of the first conjugate data, the second conjugate data, the first two pi data, and the second two pi data inverse to the identified center view, said computer further configured to weight at least one of the first conjugate data, the second conjugate data, the first two pi data, and the second two pi data with one of an inverse helical interpolation weight, an inverse-underscan weight, an inverse helical extrapolation weight, and an inverse general halfscan weight.

19. A system in accordance with claim 14 wherein to weight the first conjugate data and the second conjugate data inverse to the identified center view, said computer further configured to weight the first data sample according to:

$$w_1(\gamma, \beta) = \begin{cases} \left(\dfrac{\beta - \beta 2 + 2\pi}{\beta 1 - \beta 2 + 2\pi}\right)\left[\dfrac{(1-2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\dfrac{\beta - \beta 2 + 2\pi}{\beta 1 - \beta 2 + 2\pi}\right)\left[\dfrac{(1-2\alpha)(\beta 0 - 2\gamma - \beta)}{\pi - 2\gamma} + \alpha\right] & \beta 0 - \pi \leq \beta \leq \beta 1 \\ \left(\dfrac{\beta 2 - \beta}{\beta 2 - \beta 1}\right)\left[\dfrac{(1-2\alpha)(\beta 0 - 2\gamma - \beta)}{\pi - 2\gamma} + \alpha\right] & \beta 1 \leq \beta < \beta 0 - 2\gamma \\ \left(\dfrac{\beta 2 - \beta}{\beta 2 - \beta 1}\right)\left[\dfrac{(1-2\alpha)(\beta - \beta 0 + 2\gamma)}{\pi + 2\gamma} + \alpha\right] & \beta 0 - 2\gamma \leq \beta < \beta 2 \end{cases}$$

and weight the second data sample according to:

$$w_2(\gamma, \beta) = \begin{cases} \left(\dfrac{\beta - \beta 1}{\beta 2 - \beta 1}\right)\left[\dfrac{(1-2\alpha)(\beta 0 - 2\gamma - \beta)}{\pi - 2\gamma}\right] & \beta 1 \leq \beta \leq \beta 0 - 2\gamma \\ \left(\dfrac{\beta - \beta 1}{\beta 2 - \beta 1}\right)\left[\dfrac{(1-2\alpha)(\beta - \beta 0 + 2\gamma)}{\pi + 2\gamma} + \alpha\right] & \beta 0 - 2\gamma \leq \beta < \beta 2 \\ \left(\dfrac{\beta 1 + 2\pi - \beta}{\beta 1 + \pi - \beta 2}\right)\left[\dfrac{(1-2\alpha)(\beta - \beta 0 + 2\gamma)}{\pi + 2\gamma} + \alpha\right] & \beta 2 \leq \beta < \beta 0 + \pi \\ \left(\dfrac{\beta 1 + 2\pi - \beta}{\beta 1 + \pi - \beta 2}\right)\left[\dfrac{(1-2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where
- $\beta$ is a projection angle;
- $\beta 0$ is the identified center view;
- $\beta 1$ is the projection angle at which the first detector row intersects a plane of reconstruction;
- $\beta 2$ is the projection angle at which the second detector row intersects the plane of reconstruction;
- $\gamma$ is a fan angle; and
- $\alpha$ is a relative strength parameter.

20. A twin beam computerized tomographic (CT) imaging system for imaging an object, said imaging system comprising:
- a detector array;
- at least one radiation source; and
- a computer coupled to said detector array and radiation source and configured to:
  - helically twin beam scan an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;
  - identify a center view of the first conjugate data and the second conjugate data; and
  - weight the first data sample according to:

$$w_1(\gamma, \beta) = \begin{cases} \left(\frac{\beta - \beta 2 + 2\pi}{\beta 1 - \beta 2 + 2\pi}\right)\left[\frac{(1-2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\frac{\beta - \beta 2 + 2\pi}{\beta 1 - \beta 2 + 2\pi}\right)\left[\frac{(1-2\alpha)(\beta 0 - 2\gamma - \beta)}{\pi - 2\gamma} + \alpha\right] & \beta 0 - \pi \leq \beta \leq \beta 1 \\ \left(\frac{\beta 2 - \beta}{\beta 2 - \beta 1}\right)\left[\frac{(1-2\alpha)(\beta 0 - 2\gamma - \beta)}{\pi - 2\gamma} + \alpha\right] & \beta 1 \leq \beta < \beta 0 - 2\gamma \\ \left(\frac{\beta 2 - \beta}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \end{cases}$$

and weight the second data sample according to:

$$w_2(\gamma, \beta) = \begin{cases} \left(\frac{\beta - \beta 1}{\beta 2 - \beta 1}\right)\left[\frac{(1-2\alpha)(\beta 0 - 2\gamma - \beta)}{\pi - 2\gamma}\right] & \beta 1 \leq \beta \leq \beta 0 - 2\gamma \\ \left(\frac{\beta - \beta 1}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \\ \left(\frac{\beta 1 + 2\pi - \beta}{\beta 1 + \pi - \beta 2}\right)\left[\frac{(1-2\alpha)(\beta - \beta 0 + 2\gamma)}{\pi + 2\gamma} + \alpha\right] & \beta 2 \leq \beta < \beta 0 + \pi \\ \left(\frac{\beta 1 + 2\pi - \beta}{\beta 1 + \pi - \beta 2}\right)\left[\frac{(1-2\alpha)(\beta 0 - 2\gamma - \beta + 2\pi)}{\pi - 2\gamma} + \alpha\right] & \beta 0 + \pi \leq \beta < \beta 1 + 2\pi \end{cases}$$

where
- β is a projection angle;
- β0 is the identified center view;
- β1 is the projection angle at which the first detector row intersects a plane of reconstruction;
- β2 is the projection angle at which the second detector row intersects the plane of reconstruction;
- γ is a fan angle; and
- α is a relative strength parameter.

21. A computer readable medium encoded with a program executable by a computer for reconstructing a three-dimensional dataset representative of an imaged object, said program configured to instruct the computer to:
- helically twin beam scan an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;
- identify a center view of the first conjugate data and the second conjugate data;
- weight at least one of the first conjugate data, the second conjugate data, the first two pi data, and the second two pi data inverse to the identified center view; and
- filter and backproject the weighted projection data to generate an image of the object.

22. A computer readable medium in accordance with claim 21 wherein to identify a center view, said program further configured identify a center view wherein the center view is π/p from β1 and π/p from β2, wherein p is a helical pitch, β1 is the projection angle at which the first detector row intersects a plane of reconstruction, and β2 is the projection angle at which the second detector row intersects the plane of reconstruction.

23. A computer readable medium in accordance with claim 21 wherein to weight at least one of the first conjugate data, the second conjugate data, the first two pi data, and the second two pi data inverse to the identified center view, said program further configured to weight the first data sample according to:

$$w_1(\gamma, \beta) = \begin{cases} \left(\frac{\beta - \beta 2 + 2\pi}{\beta 1 - \beta 2 + 2\pi}\right)\left[\frac{(1-2\alpha)(\beta + 2\pi - \beta 0 + 2\gamma)}{\pi + 2\gamma} + \alpha\right] & \beta 2 - 2\pi \leq \beta \leq \beta 0 - \pi \\ \left(\frac{\beta - \beta 2 + 2\pi}{\beta 1 - \beta 2 + 2\pi}\right)\left[\frac{(1-2\alpha)(\beta 0 - 2\gamma - \beta)}{\pi - 2\gamma} + \alpha\right] & \beta 0 - \pi \leq \beta \leq \beta 1 \\ \left(\frac{\beta 2 - \beta}{\beta 2 - \beta 1}\right)\left[\frac{(1-2\alpha)(\beta 0 - 2\gamma - \beta)}{\pi - 2\gamma} + \alpha\right] & \beta 1 \leq \beta < \beta 0 - 2\gamma \\ \left(\frac{\beta 2 - \beta}{\beta 2 - \beta 1}\right)\left[\frac{(1-2\alpha)(\beta - \beta 0 + 2\gamma)}{\pi + 2\gamma} + \alpha\right] & \beta 0 - 2\gamma \leq \beta < \beta 2 \end{cases}$$

where
- β is a projection angle;
- β0 is the identified center view;
- β1 is the projection angle at which the first detector row intersects a plane of reconstruction;

β2 is the projection angle at which the second detector row intersects the plane of reconstruction;

γ is a fan angle; and

α is a relative strength parameter.

24. A computer readable medium in accordance with claim 21 wherein said computer further configured to weight the first conjugate data and the second conjugate data inverse to the identified center view.

25. A computer readable medium in accordance with claim 24 wherein to weight the second conjugate data inverse to the identified center view, said program further configured to weight the second data sample according to:

$$w_2(\gamma, \beta) = \begin{cases} \left(\frac{\beta-\beta_1}{\beta_2-\beta_1}\right)\left[\frac{(1-2\alpha)(\beta_0-2\gamma-\beta)}{\pi-2\gamma}\right] & \beta_1 \le \beta \le \beta_0 - 2\gamma \\ \left(\frac{\beta-\beta_1}{\beta_2-\beta_1}\right)\left[\frac{(1-2\alpha)(\beta-\beta_0+2\gamma)}{\pi+2\gamma}+\alpha\right] & \beta_0 - 2\gamma \le \beta < \beta_2 \\ \left(\frac{\beta_1+2\pi-\beta}{\beta_1+\pi-\beta_2}\right)\left[\frac{(1-2\alpha)(\beta-\beta_0+2\gamma)}{\pi+2\gamma}+\alpha\right] & \beta_2 \le \beta < \beta_0 + \pi \\ \left(\frac{\beta_1+2\pi-\beta}{\beta_1+\pi-\beta_2}\right)\left[\frac{(1-2\alpha)(\beta_0-2\gamma-\beta+2\pi)}{\pi-2\gamma}+\alpha\right] & \beta_0 + \pi \le \beta < \beta_1 + 2\pi \end{cases}$$

where

β is a projection angle;

β0 is the identified center view;

β1 is the projection angle at which the first detector row intersects a plane of reconstruction;

β2 is the projection angle at which the second detector row intersects the plane of reconstruction;

γ is a fan angle; and

α is a relative strength parameter.

26. A computer readable medium in accordance with claim 23 wherein α is between approximately 0 and approximately 0.5.

27. A computer readable medium in accordance with claim 25 wherein α is between approximately 0 and approximately 0.5.

28. A computer readable medium in accordance with claim 21 wherein to weight at least one of the first conjugate data, the second conjugate data, the first two pi data, and the second two pi data inverse to the identified center view, said program further configured to weight at least one of the first conjugate data, the second conjugate data, the first two pi data, and the second two pi data with one of an inverse helical interpolation weight, an inverse-underscan weight, an inverse helical extrapolation weight, and an inverse general halfscan weight.

29. A computer readable medium in accordance with claim 24 wherein to weight the first conjugate data and the second conjugate data inverse to the identified center view, said program further configured to weight the first data sample according to:

$$w_1(\gamma, \beta) = \begin{cases} \left(\frac{\beta-\beta_2+2\pi}{\beta_1-\beta_2+2\pi}\right)\left[\frac{(1-2\alpha)(\beta+2\pi-\beta_0+2\gamma)}{\pi+2\gamma}+\alpha\right] & \beta_2 - 2\pi \le \beta \le \beta_0 - \pi \\ \left(\frac{\beta-\beta_2+2\pi}{\beta_1-\beta_2+2\pi}\right)\left[\frac{(1-2\alpha)(\beta_0-2\gamma-\beta)}{\pi-2\gamma}+\alpha\right] & \beta_0 - \pi \le \beta \le \beta_1 \\ \left(\frac{\beta_2-\beta}{\beta_2-\beta_1}\right)\left[\frac{(1-2\alpha)(\beta_0-2\gamma-\beta)}{\pi-2\gamma}+\alpha\right] & \beta_1 \le \beta < \beta_0 - 2\gamma \\ \left(\frac{\beta_2-\beta}{\beta_2-\beta_1}\right)\left[\frac{(1-2\alpha)(\beta-\beta_0+2\gamma)}{\pi+2\gamma}+\alpha\right] & \beta_0 - 2\gamma \le \beta < \beta_2 \end{cases}$$

and weight the second data sample according to:

$$w_2(\gamma, \beta) = \begin{cases} \left(\frac{\beta-\beta_1}{\beta_2-\beta_1}\right)\left[\frac{(1-2\alpha)(\beta_0-2\gamma-\beta)}{\pi-2\gamma}\right] & \beta_1 \le \beta \le \beta_0 - 2\gamma \\ \left(\frac{\beta-\beta_1}{\beta_2-\beta_1}\right)\left[\frac{(1-2\alpha)(\beta-\beta_0+2\gamma)}{\pi+2\gamma}+\alpha\right] & \beta_0 - 2\gamma \le \beta < \beta_2 \\ \left(\frac{\beta_1+2\pi-\beta}{\beta_1+\pi-\beta_2}\right)\left[\frac{(1-2\alpha)(\beta-\beta_0+2\gamma)}{\pi+2\gamma}+\alpha\right] & \beta_2 \le \beta < \beta_0 + \pi \\ \left(\frac{\beta_1+2\pi-\beta}{\beta_1+\pi-\beta_2}\right)\left[\frac{(1-2\alpha)(\beta_0-2\gamma-\beta+2\pi)}{\pi-2\gamma}+\alpha\right] & \beta_0 + \pi \le \beta < \beta_1 + 2\pi \end{cases}$$

where

β is a projection angle;

β0 is the identified center view;

β1 is the projection angle at which the first detector row intersects a plane of reconstruction;

β2 is the projection angle at which the second detector row intersects the plane of reconstruction;

γ is a fan angle; and

α is a relative strength parameter.

30. A computer readable medium encoded with a program executable by a computer for reconstructing a three-dimensional dataset representative of an imaged object, said program configured to instruct the computer to:

helically twin beam scan an object at a selected pitch to acquire a first data sample from a first detector row and a second data sample from a second detector row, the first data sample comprising first conjugate data and first two pi data, the second data sample comprising second conjugate data and second two pi data, the first conjugate data and the second conjugate data are conjugate each other, the first two pi data and the second two pi data are two π projection angle apart;

identify a center view of the first conjugate data and the second conjugate data; wherein the center view is π/p from a first projection region and π/p from a third projection region, wherein p is a helical pitch; and weight the first data sample according to:

$$w_1(\gamma, \beta) = \begin{cases} \left(\dfrac{\beta - \beta2 + 2\pi}{\beta1 - \beta2 + 2\pi}\right)\left[\dfrac{(1-2\alpha)(\beta + 2\pi - \beta0 + 2\gamma)}{\pi + 2\gamma} + \alpha\right] & \beta2 - 2\pi \leq \beta \leq \beta0 - \pi \\ \left(\dfrac{\beta - \beta2 + 2\pi}{\beta1 - \beta2 + 2\pi}\right)\left[\dfrac{(1-2\alpha)(\beta0 - 2\gamma - \beta)}{\pi - 2\gamma} + \alpha\right] & \beta0 - \pi \leq \beta \leq \beta1 \\ \left(\dfrac{\beta2 - \beta}{\beta2 - \beta1}\right)\left[\dfrac{(1-2\alpha)(\beta0 - 2\gamma - \beta)}{\pi - 2\gamma} + \alpha\right] & \beta1 \leq \beta < \beta0 - 2\gamma \\ \left(\dfrac{\beta2 - \beta}{\beta2 - \beta1}\right)\left[\dfrac{(1-2\alpha)(\beta - \beta0 + 2\gamma)}{\pi + 2\gamma} + \alpha\right] & \beta0 - 2\gamma \leq \beta < \beta2 \end{cases}$$

and weight the second data sample according to:

$$w_2(\gamma, \beta) = \begin{cases} \left(\dfrac{\beta - \beta1}{\beta2 - \beta1}\right)\left[\dfrac{(1-2\alpha)(\beta0 - 2\gamma - \beta)}{\pi - 2\gamma}\right] & \beta1 \leq \beta \leq \beta0 - 2\gamma \\ \left(\dfrac{\beta - \beta1}{\beta2 - \beta1}\right)\left[\dfrac{(1-2\alpha)(\beta - \beta0 + 2\gamma)}{\pi + 2\gamma} + \alpha\right] & \beta0 - 2\gamma \leq \beta < \beta2 \\ \left(\dfrac{\beta1 + 2\pi - \beta}{\beta1 + \pi - \beta2}\right)\left[\dfrac{(1-2\alpha)(\beta - \beta0 + 2\gamma)}{\pi + 2\gamma} + \alpha\right] & \beta2 \leq \beta < \beta0 + \pi \\ \left(\dfrac{\beta1 + 2\pi - \beta}{\beta1 + \pi - \beta2}\right)\left[\dfrac{(1-2\alpha)(\beta0 - 2\gamma - \beta + 2\pi)}{\pi - 2\gamma} + \alpha\right] & \beta0 + \pi \leq \beta < \beta1 + 2\pi \end{cases}$$

where $\beta$ is a projection angle;

$\beta0$ is the identified center view;

$\beta1$ is the projection angle at which the first detector row intersects a plane of reconstruction;

$\beta2$ is the projection angle at which the second detector row intersects the plane of reconstruction;

$\gamma$ is a fan angle; and $\alpha$ is a relative strength parameter.

* * * * *

UNITED STATES PATENT AND TRADEMARK OFFICE
CERTIFICATE OF CORRECTION

PATENT NO. : 6,404,842 B1  Page 1 of 2
DATED : June 11, 2002
INVENTOR(S) : Jiang Hsieh It is certified that error appears in the above-identified patent and that said Letters Patent is hereby corrected as shown below:

Column 10,
First line of formula delete "]" insert therefor -- $+\alpha$] --.

Column 11,
First line of formula delete "]" insert therefor -- $+\alpha$] --.
Line 23, delete "$\beta 1$" insert therefor -- $\beta 2$ --.
Line 46, delete "$\beta/p$ from $\beta 1$" insert therefor -- $\pi/p$ from $\beta 1$ --.

Column 12,
First line of formula delete "]" insert therefor -- $+\alpha$] --.

Column 13,
First line of formula delete "]" insert therefor -- $+\alpha$] --.

Column 14,
First line of second formula delete "]" insert therefor -- $+\alpha$] --.

Column 15,
First line of second formula delete "]" insert therefor -- $+\alpha$] --.

Column 17,
First line of formula delete "]" insert therefor -- $+\alpha$] --.

Column 18,
First line of second formula delete "]" insert therefor -- $+\alpha$] --.

UNITED STATES PATENT AND TRADEMARK OFFICE
CERTIFICATE OF CORRECTION

PATENT NO. : 6,404,842 B1
DATED : June 11, 2002
INVENTOR(S) : Jiang Hsieh

It is certified that error appears in the above-identified patent and that said Letters Patent is hereby corrected as shown below:

Column 19,
First line of second formula delete "]" insert therefor -- +α] --.

Signed and Sealed this

Twenty-seventh Day of January, 2004

JON W. DUDAS
*Acting Director of the United States Patent and Trademark Office*